(12) United States Patent
Schlaf et al.

(10) Patent No.: US 8,598,511 B1
(45) Date of Patent: Dec. 3, 2013

(54) CARBON NANOTUBE ANCHOR FOR MASS SPECTROMETER

(75) Inventors: Rudiger Schlaf, Tampa, FL (US); Joshua Schumacher, Holiday, FL (US)

(73) Assignee: University of South Florida, Tampa, FL (US)

( * ) Notice: Subject to any disclaimer, the term of this patent is extended or adjusted under 35 U.S.C. 154(b) by 478 days.

(21) Appl. No.: 12/398,710

(22) Filed: Mar. 5, 2009

Related U.S. Application Data

(60) Provisional application No. 61/033,909, filed on Mar. 5, 2008.

(51) Int. Cl.
G21K 5/04 (2006.01)

(52) U.S. Cl.
USPC ............................. 250/282; 250/281; 250/288

(58) Field of Classification Search
USPC ........................................................ 250/282
See application file for complete search history.

(56) References Cited

U.S. PATENT DOCUMENTS

| | | | |
|---|---|---|---|
| 6,287,872 B1 | 9/2001 | Schurenberg et al. | |
| 6,670,609 B2 | 12/2003 | Franzen et al. | |
| 6,858,197 B1 * | 2/2005 | Delzeit | 423/447.3 |
| 6,900,061 B2 | 5/2005 | Smirnov et al. | |
| 6,952,011 B2 | 10/2005 | Brown et al. | |
| 6,956,209 B2 | 10/2005 | DiCesare | |
| 7,095,018 B2 | 8/2006 | Barnes et al. | |
| 7,170,052 B2 | 1/2007 | Furutani et al. | |
| 7,173,241 B2 | 2/2007 | DiCesare | |
| 7,244,407 B2 * | 7/2007 | Chen et al. | 423/445 B |
| 7,256,394 B2 | 8/2007 | Yang et al. | |
| 7,492,088 B2 * | 2/2009 | Jang et al. | 313/496 |
| 2004/0217277 A1 * | 11/2004 | Goodley et al. | 250/288 |
| 2005/0032236 A1 | 2/2005 | Axelsson | |
| 2006/0097150 A1 * | 5/2006 | Joyce et al. | 250/288 |

OTHER PUBLICATIONS

Ren, Z. F., Huangm Z. P., Xu, J. W., Wang, D. Z. and Wang, J. H. 1999. "Large Arrays of Well-Aligned Carbon Nanotubes." Proceedings of 13th International Winter School on Electronic Properties of Novel Materials. pp. 263-267. Kirchberg/Tirol, Austria.
Ren, Z.F., Huang, Z. P., Xu, J. W., Wang, J. H., Bush, P., Siegal, M. P., Provencio, P. N. 1998. "Synthesis of Large Arrays of Well-Aligned Carbon Nanotubes on Glass." Science. vol. 282. pp. 1105-1107.
Schuerenberg, M., Lubbert, C., Eickhoff, H., Kalkum, M., Lehrach, H. and Nordoff, E. 2000. "Prestructured MALDI-MS Sample Supports." Analytical Chemistry. vol. 72. No. 15. pp. 3436-3442.

(Continued)

Primary Examiner — Phillip A Johnston
(74) Attorney, Agent, or Firm — Robert J. Varkonyi; Smith & Hopen, P.A.

(57) ABSTRACT

This invention enables a sensitivity enhancement in the detection of molecular compounds. A mass spectrometry analyte support with nanotube anchors are used to concentrate MALDI samples, specifically samples prepared with water-insoluble matrix compounds, on the anchor spot. The surface structure is established through patterned carbon nanotube anchor growth, providing a nucleation center for analyte and reducing sample precipitation on the surrounding MALDI wafer. Also disclosed is a method of creating a mass spectrometry support using patterned metal catalyst to grow carbon nanotubes. The carbon nanotubes enhance nucleation on specific areas of a sample plate to concentrate analyte/matrix deposit during droplet evaporation.

8 Claims, 6 Drawing Sheets

(56) References Cited

OTHER PUBLICATIONS

Nordoff, E., Schurenberg, M., Thiele, G., Lubbert, C., Kloeppel, K., Theiss, D., Lehrach, H., and Gobom, J. 2003. "Sample Preparation Protocols for MALDI-MS of Peptides and Oligonucleotides Using Prestructured Sample Supports." International Journal of Mass Spectrometry. vol. 226. pp. 163-180.

Tannu, N.S., Wu, J., Rao, V. K., Gadgil, H. S., Pabst, M.J., Gerling, I.C., and Raghow, R. 2004. "Paraffin-Wax-Coated Plates as Matrix-Assisted Laser Desorption/Ionization Sample Support for High-Throughput Identification of Proteins by Peptide Mass Fingerprinting." Analytical Biochemistry. vol. 327. pp. 222-232.

Murakami et al. 2004. "Growth of Vertically Aligned Single-Walled Carbon Nanotube Films on Quartz Substrates and Their Optical Anisotropy." Chemical Physics Letters. vol. 385. pp. 298-303.

* cited by examiner

A

Conventional "hydrophilic" anchor:

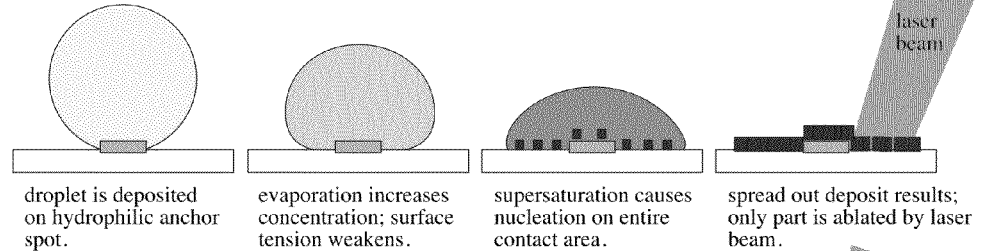

| droplet is deposited on hydrophilic anchor spot. | evaporation increases concentration; surface tension weakens. | supersaturation causes nucleation on entire contact area. | spread out deposit results; only part is ablated by laser beam. |

B

Carbon nanotube "nucleation promoting" anchor:

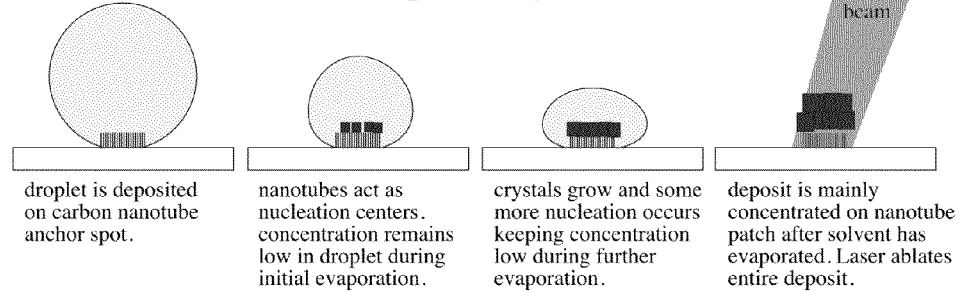

| droplet is deposited on carbon nanotube anchor spot. | nanotubes act as nucleation centers. concentration remains low in droplet during initial evaporation. | crystals grow and some more nucleation occurs keeping concentration low during further evaporation. | deposit is mainly concentrated on nanotube patch after solvent has evaporated. Laser ablates entire deposit. |

Figure 8.

CARBON NANOTUBE ANCHOR FOR MASS SPECTROMETER

CROSS REFERENCE TO RELATED APPLICATION

This application claims priority to currently pending U.S. Provisional Patent Application No. 61/033,909, entitled "Carbon Nanotube Anchor for Mass Spectrometer", filed on Mar. 5, 2008, the contents of which are herein incorporated by reference.

FIELD OF INVENTION

This invention relates to mass spectrometer sample anchors. Specifically, the invention is a carbon nanotube anchor plate for water insoluble samples in matrix assisted laser desorption ionization mass spectrometers.

BACKGROUND OF THE INVENTION

Matrix assisted laser desorption ionization mass spectrometry (MALDI-MS) is a technique used for the quantification and detection of bio-molecules and other macro-molecular substances for applications ranging from proteomics and cancer early detection to forensic investigations. Especially for proteomics and cancer research, sensitivity and analyte concentration are essential for successful measurements, since the analyte is often only available in very small quantities and/or high dilution.

The described invention aims at increasing the reproducibility and sensitivity of MALDI-MS for water-insoluble matrix based samples through improving the sample preparation process. MALDI-MS is an advanced mass spectrometry technique used to detect large molecules ("macro-molecules"). Such molecules cannot be measured using conventional mass spectrometry techniques due to fragmentation. MALDI-MS achieves ionization by proton transfer from a matrix compound (usually a crystal-forming acid) to the analyte to be analyzed. To achieve this proton transfer, the analyte needs to be embedded within the matrix compound, which generally exceeds the analyte amount by two to three magnitudes. This is achieved by creating a mixed solution of both analyte and matrix, which is drop-deposited on a sample plate. Evaporation results in a solid residue of analyte/matrix compound. This solid residue is then ablated with a laser focused into a tight (~100 μm diameter) high-intensity spot. The ablated material forms a gaseous cloud above the sample in which protons are transferred from matrix to analyte, resulting in charging of the analyte molecules, which can subsequently be analyzed in the mass spectrometer by use of electrical or magnetic fields.

The standard matrix materials used in MALDI investigations can be generally divided into water-soluble and water-insoluble compounds. The mostly used water-soluble compounds are 2,5-dihydroxybenzoic acid (2,5-DBH) and 3-hydroxypicolinic acid (3-HPA), while the most popular water-insoluble material is α-cyano-4-hydroxycinnamic acid (HCCA).

Since drop-deposition of matrix/analyte solution on a flat plate typically yields irregular circular deposits, such deposits are difficult to analyze. Usually a trial and error procedure is used to find a "sweet spot" that yields a good signal-to-noise ratio. This is time consuming, and yields poorly reproducible data. Consequently, this has led to the invention of so-called anchor plates, where arrays of small (100-800 μm diameter) hydrophilic spots are created on a hydrophobic substrate. This allows deposited droplets to anchor to the hydrophilic spots, since they are repelled by the hydrophobic surroundings. Successively, evaporation results in crystallization of the matrix/analyte deposit on or close to the hydrophilic spot. This allows a much more reproducible interrogation of the sample since the laser spot covers a larger portion of the area coated with the matrix/analyte deposit. This eliminates the hunt for the "sweet spot", while also increasing the sensitivity of the measurement due to the analyte concentration effect of the procedure (Schuerenberg, C. Luebbert, H. Eickhoff, M. Kalkum, H. Lehrach and E. Nordhoff: "Prestructured MALDI-MS sample supports", Analytical Chemistry 72 (15), pp. 3436-3442 (2000)).

This procedure works reliably with water-soluble matrix compounds such as 2,5-DHP or 3-HPA, while it does not work well with water-insoluble matrix compounds such as HCCA (Schuerenberg, C. Luebbert, H. Eickhoff, M. Kalkum, H. Lehrach and E. Nordhoff: "Prestructured MALDI-MS sample supports", Analytical Chemistry 72 (15), pp. 3436-3442 (2000); M. Schuerenberg: "AnchorChip™ Technology, Revision 2.3", Bruker Product Information, (2005)). When HCCA is used, the final deposit is spread over an area much wider than the anchor spot. The reason for this behavior lies in the necessity to use an organic solvent mixable with water to dissolve the HCCA matrix. Usually, acetonitrile is used as organic solvent since it dissolves HCCA, and it is polar enough to mix well with the aqueous solution containing the analyte to be investigated.

SUMMARY OF THE INVENTION

A mass spectrometry analyte support is disclosed which comprises at least one analyte anchor disposed on the analysis face of a support wafer. In some embodiments, the support wafer is a silicon wafer, and may optionally be coated with a hydrophobic material. The analyte anchors disposed on the support wafer at comprise a plurality of nanotubes, which may be carbon nanotubes. Thus a plurality of carbon nanotube based anchoring spots are located on the silicon support for organic solvent containing MALDI samples, which result in the concentration of water-insoluble matrix based MALDI samples on a suitable anchor spot.

When HCCA is used, the final deposit is spread over an area much wider than the anchor spot. The reason for this behavior lies in the necessity to use an organic solvent mixable with water to dissolve the HCCA matrix. Usually, acetonitrile is used as organic solvent since it dissolves HCCA, and it is polar enough to mix well with the aqueous solution containing the analyte to be investigated. Since the organic solvent has a higher vapor pressure than water, it evaporates first after the droplet is deposited. This creates a supersaturation situation for the matrix molecules, causing them to precipitate on the area surrounding the anchor spot since the drop is still relatively large at that point, while in the same time collapsing due to the increased concentration. At the end of the evaporation process an area much larger than that of the anchor spot is coated with deposit, similar to drop depositions on a standard (non-anchor stainless steel) plate. On such a deposit the laser spot can again only interrogate a small fraction of the total deposit. Hence most of the analyte is never analyzed by the mass spectrometer, limiting the total achievable sensitivity.

The invention addresses this issue by introducing an additional feature to provide an anchor spot more conducive to nucleation of the matrix compound than the surrounding area, and precipitation on the surrounding area due to supersaturation could be avoided. Instead, deposition would occur exclusively on the anchor spot during the initial organic solvent evaporation phase, even if the droplet covered a larger area than the anchor spot. A patch of aligned carbon nanotubes are grown by plasma enhanced chemical vapor deposition (PECVD) on a standard Si wafer (other substrates could be used) thereby generating an anchoring spot. This technique is an established technique originally invented by Z. F. Ren et al. (Z. F. Ren, Z. P. Huang, J. W. Xu, D. Z. Wang, J. H. Wang, L. Calvet, J. Chen, J. F. Klemic and M. A. Reed: "Large Arrays of Well-Aligned Carbon Nanotubes", (1999), Electronic Properties of Novel Materials—Science and Technology of Molecular Nanostructures, pp. 263-267). This technique uses a catalyst (usually Ni) to enable carbon nanotube growth. Patterning of the catalyst allows the definition of areas with and without nanotube growth. This was utilized for the invention through mask-based patterning of 150 μm diameter Ni patches subsequently subjected to PECVD growth of nanotubes (the size of the patches is only limited by the patterning resolution available). Our experiments have shown that such nanotube arrays act as anchoring surfaces for analyte/water-insoluble matrix solutions (for pure water carbon nanotubes actually act as hydrophobic surfaces, probably due to the higher surface tension of pure water), thereby anchoring the deposited drop since the nanotube spot is surrounded by hydrophobic native Si oxide.

Carbon nanotube spots not only anchor the deposited drop, but they also act as nucleation centers causing early nucleation of the analyte/matrix compound on top of the nanotube array as the droplet evaporates. This prevents supersaturation of the solution, and therefore strongly reduces deposition on areas surrounding the nanotube spots (see below for further description). This effect may also be achieved with other materials that form a similar surface morphology. Examples include, semiconductor or insulator nanowires, or micromachined/lithographically patterned three dimensional surface structures. In some embodiments, these nanotubes are aligned with the other nanotubes, and specifically may be carbon nanotubes aligned with the other carbon nanotubes.

Also disclosed in a method of creating a mass spectrometry analyte support. A metal catalyst is deposited on the analysis face of a MALDI support wafer, such as a silicon wafer. The metal catalyst is then patterned to form seeds for subsequent nanotube growth. The ambient pressure surrounding the support wafer is reduced and the wafer exposed to ammonia and a carbon source. During deposition of the metal catalyst, the catalyst may optionally be annealed to the support wafer by warming the support wafer-metal catalyst at 200° C. for 24 hours. Exemplary metal catalyst include iron, iron and molybdenum, cobalt, cobalt and molybdenum, and nickel. In certain embodiments, the metal catalyst is applied to the support wafer at 10 nm to 40 nm thick.

The metal catalyst seeds are patterned as is known in the art, such as lithographic patterning. The carbon source may be any known to form nanotubes, such as methane, carbon oxides (both dioxide and monoxide), hexane, acetylene and ethanol. A useful carbon source is gaseous acetylene.

Also disclosed is a method of analyzing an analyte sample. A water-insoluble matrix, such as HCCA, is first dissolved in an organic solvent, such as acetonitrile, and analyte added to the matrix-solution. The dissolved analyte-matrix solution is then applied to the mass spectrometry analyte support, described above. The dissolved analyte-matrix solution is nucleated on the support wafer, such as by allowing the solution to evaporate, thereby forming concentrated analyte locales on the nanotube anchors. In certain embodiments, the nanotube anchors are aligned carbon nanotubes.

The analyte-matrix solutes remaining from the analyte-matrix solution are lased, producing a gas which is then analyzed. The sample may be lased using a nitrogen laser, however any lasers known in the art for use in mass spectrometry analysis may be used in this invention.

The inventions disclosed herein were tested using drop-deposition of identical 0.2 μL aliquots of 250 fmol/μL peptide standard solution (Mariner CALMIX 1-consisting of des-Arginine-Bradykinin, Angiotensin I, Glu-Fibrinopeptide, and Adrenocorticotropic Hormone (ACTH); Applied Biosystems (Foster City, Calif.)) mixed with HCCA matrix compound at a strength of 3 mg/ml on a conventional Bruker "anchor plate" (M. Schuerenberg: "AnchorChip™ Technology, Revision 2.3", Bruker Product Information, (2005)), and on the invention, a carbon nanotube based "nucleation enhancing" anchor spot. It was noted that the experiment on the nanotube spot had a slightly different matrix concentration of 2.5 mg/ml. The analyte deposit was analyzed for the conventional anchor sample plate, where a 200 μm diameter anchor spot was visible in the top left quadrant of the deposited residue, indicated by a circle. Of particular note, the matrix/analyte deposit was considerably larger (~0.8 mm diameter) than the anchor spot. In contrast, deposition on the carbon nanotube anchor spot resulted in an almost complete concentration of the analyte/matrix crystals onto the ~150 μm diameter nanotube area, where most of the deposit is crystallized on top of the carbon nanotubes. This nucleation enhancement may be achieved with other materials, such as semiconductor or insulator nanowires, or micromachined/lithographically patterned three dimensional surface structures.

BRIEF DESCRIPTION OF THE DRAWINGS

For a fuller understanding of the invention, reference should be made to the following detailed description, taken in connection with the accompanying drawings, in which:

FIGS. 8(a) and (b) are schematic depictions of crystallization processes (A) on standard hydrophilic anchor, and (B) on nucleation promoting anchor spot. The nucleation promoting anchor keeps the analyte/matrix concentration of the droplet nearly constant during evaporation of the solvent through early nucleation on the anchor spot. This prevents deposition of solids in areas outside the anchor spot.

DETAILED DESCRIPTION OF THE PREFERRED EMBODIMENT

Disclosed is a mass spectrometry analyte support, which is useful in performing various analysis procedures, such as MALDI-TOF. The device promotes the nucleation of analyte on a discrete location on the analyte support, increasing sensitivity and consistency and decreasing analysis time.

Figure 1:
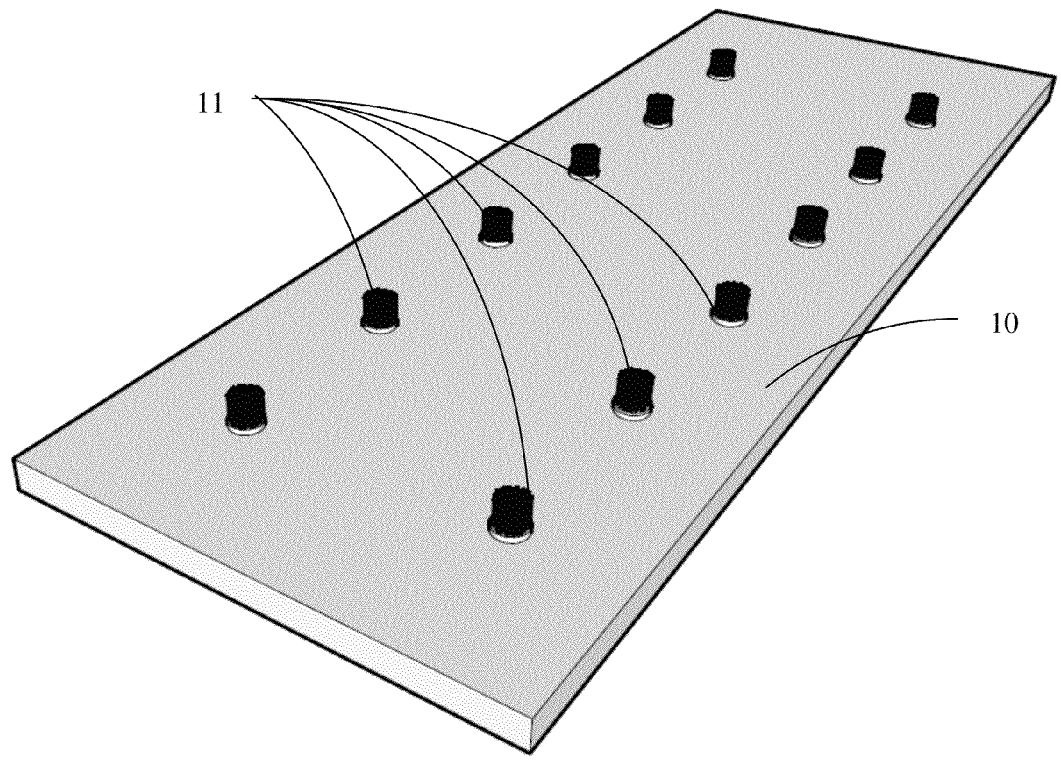
FIG. 1 is an isometric view of the target support wafer of the present invention. The carbon nanotubes have an increased size compared to the wafer to allow visualization of the nanotubes.

A vital element of mass spectrometers, such as MALDI, are target support 10. Anchor spot 11 is developed on target support 10, and is designed to hold or maintain a target 20, seen in FIG. 1. Target support 10 may comprise or be coated with a hydrophobic material, as is known in the art.

Carbon nanotubes are extremely hydrophobic and have the capability of absorbing UV energy. These characteristics of carbon nanotubes enhance MALDI detection and enable matrixless biomolecular detection. The carbon nanotube material creates a surface for improved ionization or production of ion plume, at least in part from the hydrophobic nature of the carbon nanotube surface. After the growth of carbon nanotubes, the anchor spots becomes slightly roughened and provide large surface areas that promote the crystallization of analyte and matrix. Carbon nanotubes provide not only a hydrophobic anchor, but a large surface area with strong absorption at 334 nm.

Carbon nanotubes grow on a layer of transition metal catalyst pre-deposited on a substrate at optimal temperature and pressure or transition metal catalytic clusters. Carbon nanotubes can also be directly coated on a chemically modified surface. There are a number of techniques for the preparation of carbon nanotubes. For instance, single walled carbon nanotubes have been prepared as discussed by Ericson et al., Chem. Mater. 2003, 15, 175-178, 2003; Huang, Z. P., Applied Physics Letters, Volume 82, Number 3, Jan. 20, 2003; Melosh et al., Science, Volume 300, Apr. 4, 2003; Chen, R. J., J. Am. Chem. Soc. 2001, 123, 3838-3839; Bradley, K, NanoLetters Vol. 0. No. 0 A-D, Nov. 5, 2003; Lustig, S. R., Nanoletters, Vol. 3, No. 8, 1007-1012, 2003). Carbon nanotubes can be synthesized and grown by various techniques, including High Pressure CO Conversion (HiPCO), Pulsed-Laser Vaporization (PLV), Arc Discharge, and Chemical Vapor Deposition (CVD). The first three methods only produce tangled nanotubes mixed with byproduct. The chemical vaporization technique provides the best methodology to obtain ordered and controlled carbon nanotube density with relatively pure carbon nanotubes. H. Dai, ACC. Chem. Res. 2002, 35, 1035-1044; R. Saito et al, "Physical Properties of Carbon Nanotubes" Imperial College Press). Conversely, multiple walled carbon nanotubes have also been developed and employed. A number of techniques for preparing these types of nanotubes are also known in the art. Both single wall and multiwall carbon nanotubes can be aligned themselves in a defined direction. Carbon nanotubes largely comprise a ring structure organized in a variety of ways. For instance, they may be ordered at the atomic level as well as to form larger ordered structures and/or supramolecular structures. These various ordered structures are applicable to the present invention and improve over the prior art in providing more efficient ion plume. Other methods and techniques known and developed in the art may be employed.

Chemical vapor deposition (CVD) uses hydrocarbon gases, such as $CH_4$, CO, $C_6H_6$, and $C_2H_5OH$, as a carbon stock with metal catalysts, like Fe, Fe/Mo, Co, Co/Mo, and Ni, as a "seed" to grow carbon nanotubes at 500° C.-1200° C. The distribution, density and location of these seeds determined the resulting carbon nanotube density and location. Seeds can be controlled using polymer carrier approaches, and lithography. In these approaches, a polymer is employed as a binder to disperse a catalyst uniformly across the wafer by a spin coating method. Catalysts can be either attached or otherwise complexed to the repeat unit of one segment of a polymer or one of the homopolymer constituents. The size of catalyst cluster, i.e. seed, after polymer removal is determined by the catalyst-containing chain length. Spacing between seeds is determined by the dilution factor, the volume ratio of polymer segments or by lithography, with distance between seeds determined by electron beam or optical lithography. Through this approach, the population of carbon nanotubes can be controlled precisely and also the carbon nanotube size.

Carbon nanotubes can also be grown using a related dispersion approach. For instance, 0.2 wt % Ni may be spun or sputtered onto a silicon dioxide wafer surface followed by annealing at 200° C. for 24 hrs and removing the organic component. The resulting Ni catalyst is uniformly dispersed and may be defined into seeds. Treatment with a carbon source then results in nanotubes on the surface of the wafer. Other dispersion techniques and materials may be utilized such as 0.25 wt % Polystyrene-b-Poly-(ferrocenyl ethyl methyl silane), coated on a thermal oxide surface. The wafer/catalyst is calcinated at 700° C. and carbon nanotube growth performed at 900° C. under $CH_4$.

Anchor spot 11 is at least one patch of aligned carbon nanotubes, which are grown by plasma enhanced chemical vapor deposition (PECVD) on target support 10, which may be a standard silicon wafer or other conductive substrates could be used, such as metal foils. A nickel catalyst was patterned onto target support 10 at pre-determined locations of the target support. However, other catalysts include Fe and Co. The catalyst comprises a thin layer of the nickel metal catalyst sputtered onto target support using mask-based patterning or electron beam lithography and metal evaporation, resulting in a 10-25 nm layer of nickel at spot locations 12 that are 150 µm in diameter, seen in FIG. 2. The target support was then subjected to plasma-enhanced chemical vapor deposition (PECVD). The target support was placed in a vacuum container and the ambient pressure reduced to below $1 \times 10^{-3}$ Torr. Then the substrate was heated to approximately 600° C. Ammonia was added to the vacuum container at 200 standard cubic centimeters per minute (sccm). After approximately 30 seconds, acetylene gas was added at 50 sccm forming a mixture of 1:4 acetylene to ammonia. The reaction was allowed to commence for 30 minutes, forming a patterning of areas with and without nanotube growth. The carbon nanotubes are uniformly distributed in the seeded surface of the wafer. The carbon nanotubes also display predictable density and ordering, as seen in the images.

Anchor spot 11 is defined as an area coated with nanotubes, which acts as an anchoring surface for analyte/water-in-soluble matrix solutions. This anchors a deposited test drop to the nanotube area, since the nanotube spot is surrounded by hydrophobic native Si oxide. In traditional MALDI samples, the test drop leaves sequential rings, formed from distinct crystallization events during evaporation of the test drop. The carbon nanotube anchor spots also advantageously provide nucleation centers causing early nucleation of the analyte/matrix compound on top of the nanotube array as the droplet evaporates. This early nucleation prevents supersaturation of the solution and reduces deposition on areas surrounding the nanotube spots.

Example 1

Prior to work with nonpolar matrices, such as HCCA, 3-HPA (water soluble) matrix was tested on a carbon nanotube enhanced substrate. A concentrating effect was witnessed with the carbon nanotube substrate, however it was similar to what can be observed using commercial anchor plates.

Example 2

Figure 3:
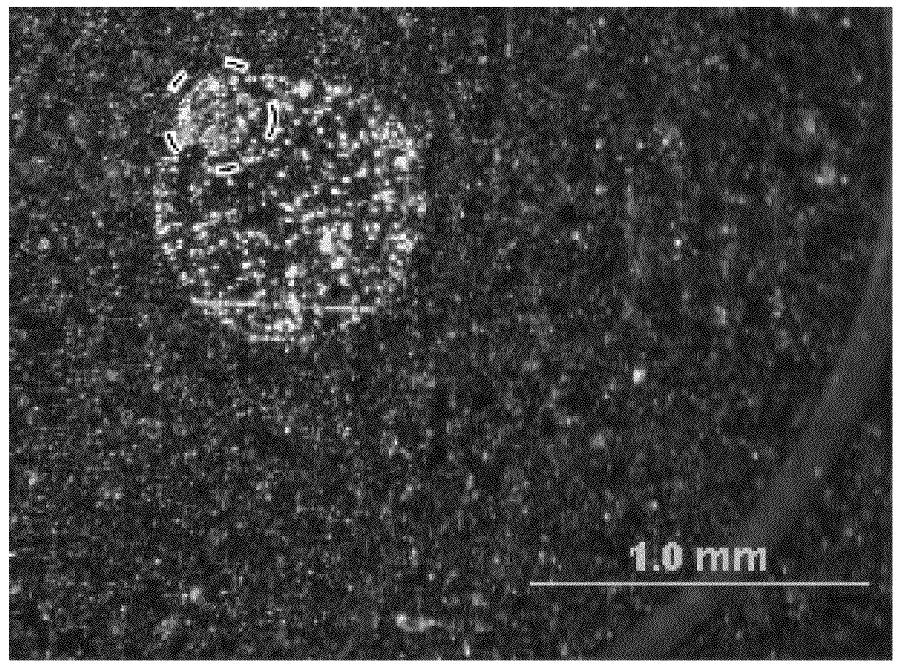
FIG. 3 depicts a solution of 250 fmol peptide standard in 3 mg/ml HCCA matrix compound deposited MALDI samples on standard "anchor-plate" (Bruker). A ~0.8 mm diameter deposition area occurred encompassing the anchor spot (circled on top left), but considerably exceeding it.

Analyte/matrix crystallization was compared on traditional target supports versus carbon nanotube-seeded target supports. 0.2 µL aliquots of 250 fmol/µL Mariner CALMIX 1 peptide standard solution (des-Arginine-Bradykinin, Angiotensin I, Glu-Fibrinopeptide, and Adrenocorticotropic Hormone (ACTH); Applied Biosystems (Foster City, Calif.)) mixed in a 3 mg/ml HCCA matrix compound was dropped onto a conventional Bruker "anchor plate" and allowed to evaporate. SEM images of the resulting solid matrix/analyte deposits display a diffuse 200 µm diameter anchor spot residue, seen in FIG. 3. Matrix concentrations were varied proportionally with the analyte, from 0.3 mg/mL to 0.006 mg/mL HCCA, to keep the matrix to analyte ratio constant. The matrix/analyte deposit is considerably larger (~0.8 mm diameter) than the anchor spot (circled) on the Bruker target support. It was also noted that this large matrix/analyte deposit was similar in magnitude to previous studies on MALDI matrix/analyte deposition (Schuerenberg, C. Luebbert, H. Eickhoff, M. Kalkum, H. Lehrach and E. Nordhoff: "Prestructured MALDI-MS sample supports", Analytical Chemistry 72 (15), pp. 3436-3442 (2000)).

Figure 4:
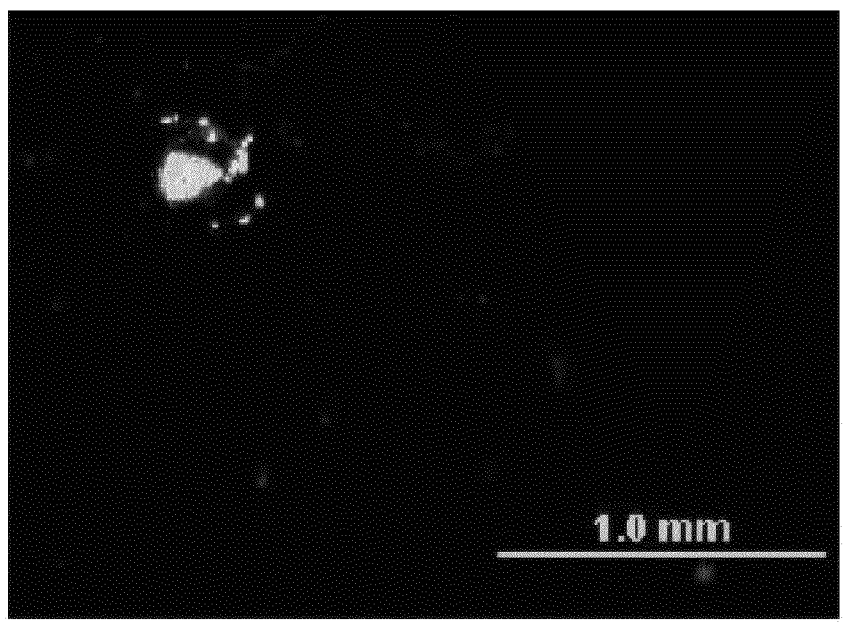
FIG. 4 depicts a solution of 250 fmol peptide standard in 2.5 mg/ml HCCA matrix compound deposited on a carbon nanotube "nucleation enhancing" anchor spot on a Si wafer. Only very few crystallites are located outside the central nanotube area due to early nucleation onset on the nanotube area.

The Mariner CALMIX 1 peptide standard solution (des-Arginine-Bradykinin, Angiotensin I, Glu-Fibrinopeptide, and Adrenocorticotropic Hormone (ACTH); Applied Biosystems (Foster City, Calif.)) was prepared again, and mixed in a 2.5 mg/ml HCCA matrix compound. 0.2 µL aliquots of 250 fmol/µL standard were dropped onto a carbon nanotube target support and allowed to evaporate. In contrast to the traditional Bruker support, deposition on the carbon nanotube anchor spot resulted in an almost complete concentration of the analyte/matrix crystals onto the ~150 µm diameter nanotube area, as seen in FIG. 4.

Figure 5:
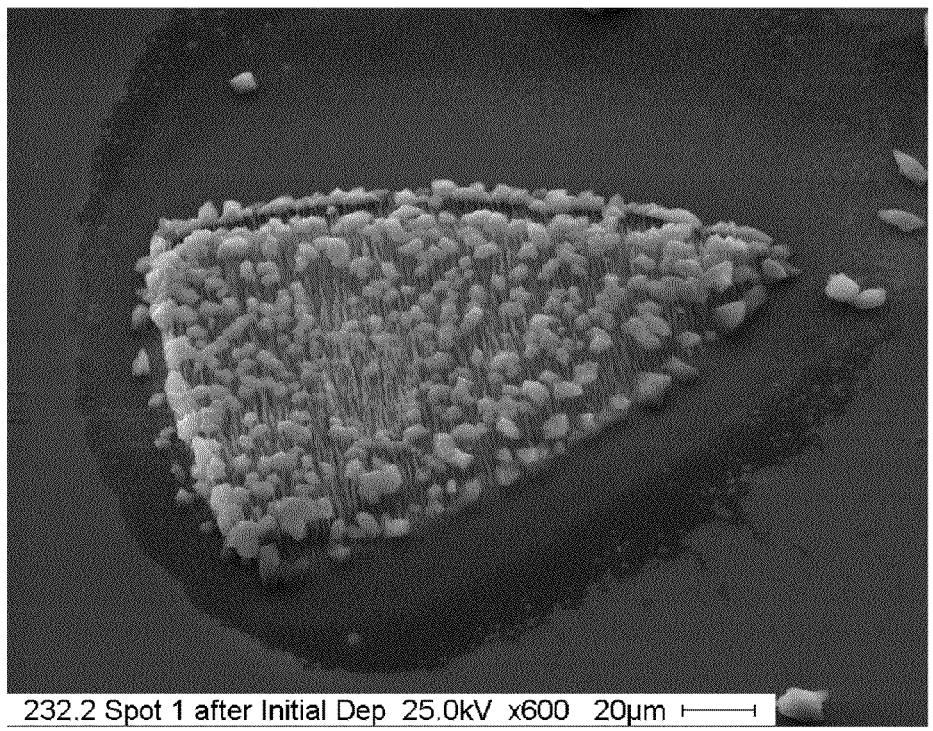
FIGS. 5(a) and (b) are scanning electron microscopy images of the carbon nanotube patch used as anchor spot. (A) The matrix/analyte preferentially crystallizes onto the carbon nanotubes and is concentrated into a ~150 μm diameter area. (B) A magnified image of matrix/analyte crystals formed on the top of the nanotubes.
Figure 5:
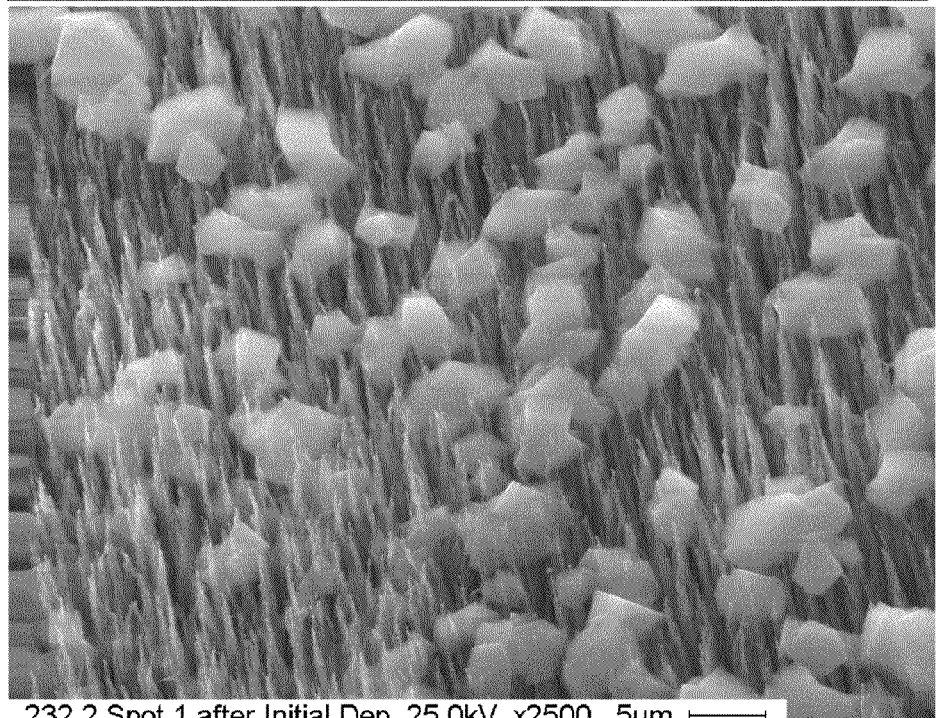

Scanning electron microscopy images were captured of the deposit on top of the carbon nanotube covered area, seen in FIGS. 5(a) and (b). As can be seen in FIG. 5(a), the area covered by the initial droplet (dark region) was significantly larger than the anchor spot. The crystallization of matrix and analyte preferentially occurred on the carbon nanotubes, with only a few crystals forming on the empty target support. Closer analysis of the anchor spot, seen in FIG. 5(b), shows the analyte/matrix crystals deposited on the peaks of the carbon nanotubes, documenting that the crystalline deposit forms on top of the carbon nanotubes.

Example 3

Figure 6:
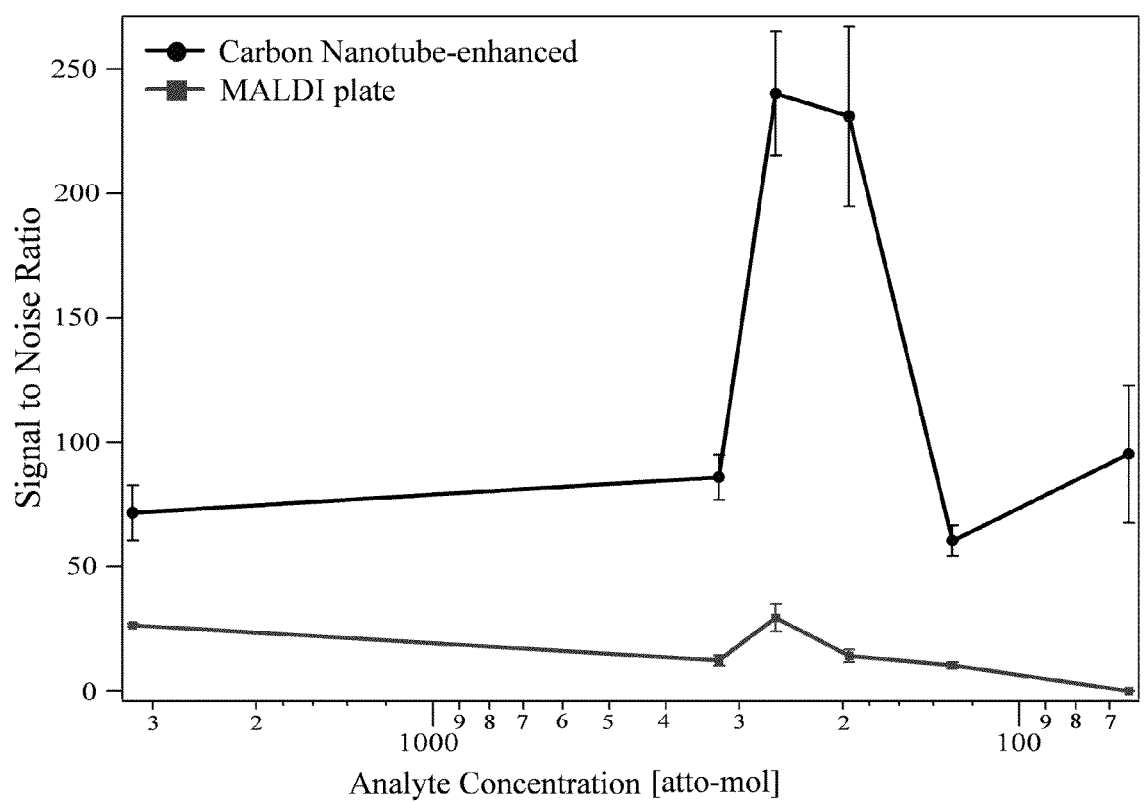
FIG. 6 is a graph comparing the MALDI-TOF-MS signal-to-noise ratio of the Glu-Fibrinopeptide 1570 m/z peak for a series of different analyte concentrations deposited on standard and carbon nanotube substrates. The nanotube substrates show consistently better signal.

Carbon nanotube anchor spots were found to vastly improve MALDI-TOF-MS signal-to-noise ratios. An Applied Biosystems Voyager DE STR MALDI-TOF and nitrogen laser at 20 Hz firing frequency with 400 micron fiber coupling were used for these experiments. Glu-Fibrinopeptide samples were then digested and mixed in a 2.5 mg/ml HCCA matrix. 0.2 µL aliquots of 250 fmol/µL were applied to either the traditional Bruker support or the carbon nanotube target support and ionized by a laser and run through a mass spectrometer with the operating laser intensity set slightly above threshold levels, and an acquisition of 250 shots per spectrum. The samples were analyzed on single positions on the target support using a delayed-extraction mode (extraction delay 200 nanoseconds). Signal-to-noise ratios for 1570 m/z peak in a variety of analyte concentrations were recorded, as seen in FIG. 6. The nanotube-based anchor spot samples display at least a 3-5× better signal than the traditional Bruker support. The reason for the much stronger (~50×) signals at the 195 and 260 attomol samples is not known, but may lead to a further increase in sensitivity.

Figure 7:
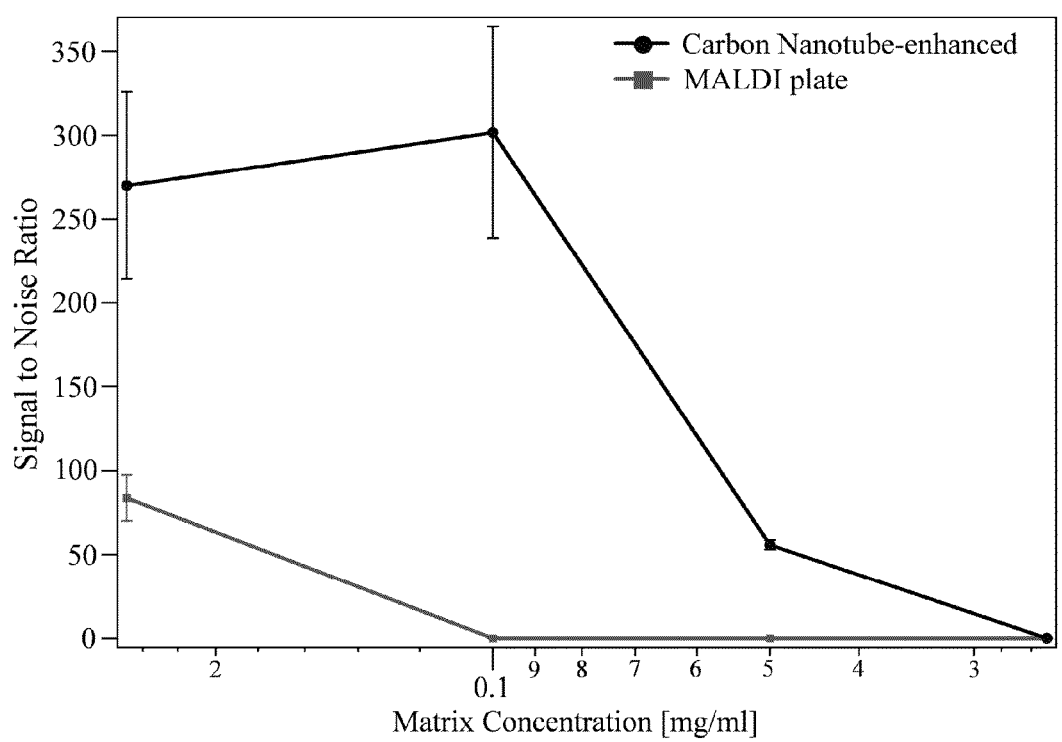
FIG. 7 is a graph comparing the MALDI-TOF-MS signal-to-noise ratio of the Glu-Fibrinopeptide 1570 m/z peak for a series of different matrix/analyte concentration ratios. The nanotube nucleation promoting anchor spots ("CNT") show consistently better signal, with the highest performance increase at lower matrix concentrations.

Moreover, at low matrix concentrations, carbon nanotube target supports greatly enhance signal-to-noise ratios compared to traditional Bruker supports, as seen in FIG. 7. Spots performances were compared for traditional Bruker supports and carbon nanotube target supports by suspending 2 fmol/µl Glu-Fibrinopeptide analyte was suspended in varying amounts of HCCA matrix from 0.25 mg/ml to 0.025 mg/ml. The matrix-to-analyte ratio was compared to signal-to-noise for both traditional Bruker supports and carbon nanotube target supports. The nanotube spots show consistently better performance than the standard plate control samples, and enhance the signal levels in samples with 0.1 mg/ml of matrix or less.

The data shown in FIGS. 6 and 7 represent the average of multiple samples that were prepared identically and investigated at the same time under the same conditions for each data point. As seen by the standard error bars of the mean for the collected data, the carbon nanotube supports significantly improve the signal to noise ration over conventional supports.

As seen in the examples, using a HCCA matrix the final deposit is spread over a much wider area than the anchor spot in traditional target supports. The reason for this behavior lies in the necessity to use an organic solvent mixable with water to dissolve the HCCA matrix. Acetonitrile is typically used as organic solvent as it dissolves HCCA and is sufficiently polar to mix with the aqueous analyte solution. The ensuing scenario after deposition is schematically shown in FIG. 8(a). The organic solvent evaporates first due to its higher vapor pressure than water, creating a supersaturation for the matrix molecules. This causes the matrix molecules to precipitate in situ around the anchor spot since the drop is still relatively large at that point, while in the same time collapsing due to the increased concentration. At the end of the evaporation process an area much larger than that of the anchor spot is coated with deposit, similar to drop depositions on a standard (non-anchor stainless steel) plate, as seen in FIG. 8(a). The MALDI laser spot can only interrogate a small fraction of the total deposit, resulting in most analyte never being analyzed by the mass spectrometer and limiting the total achievable sensitivity.

Figure 2:
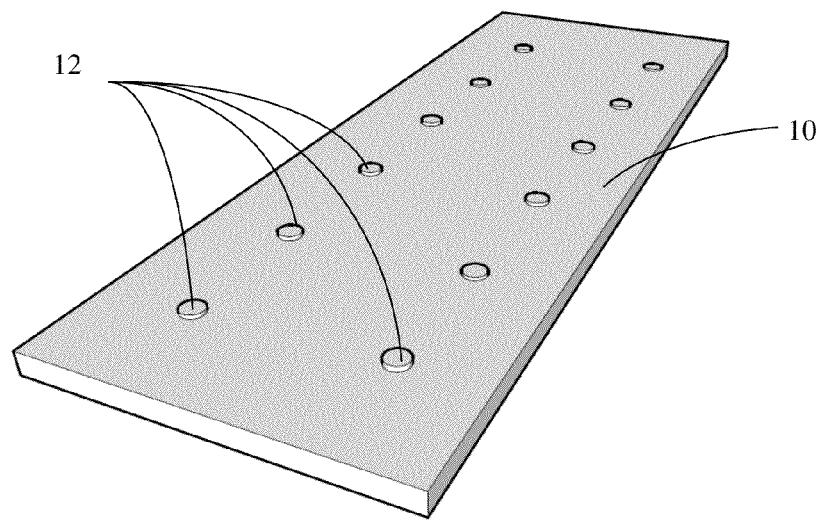
FIG. 2 is an isometric view of the target support wafer of the present invention showing the nickel catalyst seeds. The seed islands are enlarged compared to the wafer to allow visualization.

The carbon nanotubes provide an anchor spot which promotes selective nucleation of the matrix compound on the nanotube versus the surrounding area, avoiding supersaturation precipitation on the surrounding area. Deposition occurs exclusively on the anchor spot during the initial organic solvent evaporation phase, regardless of the area covered by the droplet, as seen in FIG. 8(b). This results in significant signal improvement as seen in FIG. 2. The nanotubes also demonstrated a much more reproducible analysis process. The small size of the deposit eliminates the "hunting" for signal, as every excitation from the laser yielded signal until analyte depletion occurred.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of mass spectrometer anchors, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of analyzing an analyte sample, comprising the steps of:
    dissolving a water-insoluble matrix in a mixture of water and organic solvent;
    adding an analyte to the matrix solution;
    applying the dissolved analyte-matrix solution to a mass spectrometry analyte support, wherein the mass spectrometry analyte support further comprises
        a support wafer further comprising at least an analysis face; and
        at least one analyte anchor disposed on the analysis face further comprising a plurality of nanotubes aligned perpendicularly to the analysis face;
        wherein the at least one analyte anchor has a diameter of about 150 μm to 200 μm;
    nucleating the dissolved analyte-matrix solution on the nanotubes of the support wafer;
        where the dissolved analyte preferentially nucleates on the plurality of nanotubes of the analyte support;
    lasing the plurality of nanotubes of the analyte support to ionize the nucleated analyte-matrix solution;
    analyzing the gas produced from ionized analyte-matrix solution.

2. The method of claim 1, wherein the plurality of nanotubes are aligned carbon nanotubes.

3. The method of claim 1, wherein the sample is lased using a nitrogen laser.

4. The method of claim 1, wherein the matrix is HCCA.

5. The method of claim 1, wherein the organic solvent is acetonitrile.

6. The method of claim 1, wherein the dissolved analyte-matrix solution is nucleated by allowing the solvent to evaporate.

7. The method of claim 1, wherein the matrix is 3-hydroxypicolinic acid or α-cyano-4-hydroxycinnamic acid.

8. The method of claim 1, wherein the support wafer is coated with a hydrophobic material.

* * * * *